(12) United States Patent
Iversen

(10) Patent No.: US 6,991,655 B2
(45) Date of Patent: Jan. 31, 2006

(54) COMPUTER ASSISTED INSERTION OF AN ARTIFICIAL HIP JOINT

(75) Inventor: Bjorn Franc Iversen, Humlebaek (DK)

(73) Assignee: Orthometer A/S, Horsholm (DK)

( * ) Notice: Subject to any disclaimer, the term of this patent is extended or adjusted under 35 U.S.C. 154(b) by 0 days.

(21) Appl. No.: 10/474,397

(22) PCT Filed: Apr. 8, 2002

(86) PCT No.: PCT/NO02/00137

§ 371 (c)(1),
(2), (4) Date: Mar. 18, 2004

(87) PCT Pub. No.: WO02/080824

PCT Pub. Date: Oct. 17, 2002

(65) Prior Publication Data

US 2004/0147926 A1    Jul. 29, 2004

(51) Int. Cl.
*A61F 2/32* (2006.01)
(52) U.S. Cl. .................................. 623/22.12
(58) Field of Classification Search ............ 623/22.12, 623/22.4, 22.42, 22.11; 606/99, 130
See application file for complete search history.

(56) References Cited

U.S. PATENT DOCUMENTS

| | | |
|---|---|---|
| 5,141,512 A | 8/1992 | Farmer et al. |
| 5,320,625 A | 6/1994 | Bertin |
| 5,540,697 A | 7/1996 | Rehmann et al. |
| 5,769,092 A | 6/1998 | Williamson, Jr. |
| 5,976,149 A | 11/1999 | Masini |
| 6,205,411 B1 | 3/2001 | DiGioia, III et al. |
| 2004/0181144 A1 * | 9/2004 | Cinquin et al. ............. 600/407 |

FOREIGN PATENT DOCUMENTS

| | | |
|---|---|---|
| EP | 0 207 873 B1 | 12/1989 |
| EP | 0 469 966 A1 | 2/1992 |
| EP | 0 920 838 A2 | 6/1999 |
| EP | 0 888 759 B1 | 1/2003 |
| EP | 0 865 776 B1 | 5/2003 |
| GB | 2 197 790 A | 6/1988 |
| WO | WO 91/06262 | 5/1991 |
| WO | WO 98/40037 | 9/1998 |
| WO | WO 01/19296 | 3/2001 |
| WO | WO 01/19296 A1 | 3/2001 |

OTHER PUBLICATIONS

Norwegian Search Report, Nov. 15, 2001, NO.
International Search Report, Jul. 19, 2002, WO.

* cited by examiner

*Primary Examiner*—Eduardo C. Robert
(74) *Attorney, Agent, or Firm*—Peter F. Corless; Christine C. O'Day; Edwards Angell Palmer & Dodge LLP

(57) ABSTRACT

A system and a method for ensuring correct insertion of the components of a femoral prosthesis, i.e. a prosthesis stem with a ball head and a cup with recess for receipt of the ball head, is described. The system comprises a tool for controlling the mutual angle between the prosthesis stem and the cup in addition to a positioning system for definition of a reference system and for determination and adjustment of the offset and length of the leg.

12 Claims, 5 Drawing Sheets

COMPUTER ASSISTED INSERTION OF AN ARTIFICIAL HIP JOINT

CROSS-REFERENCE TO RELATED APPLICATIONS

This application claims filing date priority benefit to Norwegian application No. 2001 1769 filed Apr. 6, 2001, and to PCT application No. PCT/NO02/00137, filed Apr. 8, 2002, under 35 U.S.C. 119 which is explicitly incorporated by reference as if set forth below.

BACKGROUND

The present invention regards the area of orthopedic surgery, and in particular a device for ensuring that prosthesis components are inserted correctly upon implantation of artificial hip joints, and to methods for doing the same.

An artificial hip joint has two main components; a prosthesis stem and a cup. One end of the prosthesis stem is provided either with a spherical ball head or a prosthesis neck on which can be placed a ball head, where the ball head is designed for a close, sliding fit in a spherical recess in the cup. Together, the prosthesis stem with the ball head and the cup will act as a ball joint to replace the natural ball joint.

The other end of the prosthesis stem comprises an elongated part designed to be attached to the hollow femoral canal in the patient's femur.

The cup is designed to be attached to the cavity on the patient's pelvis. The hemispherical shaped, recess in the cup is linked with an exterior surface designed to be attached to the pelvis, via a side face. The exterior surface may have various shapes, all according to the method of attachment to the pelvis and other choices made by the supplier. Several of the cups that are in use are shaped as an approximate hemisphere, where the outer hemispherical surface is designed to be cemented to the pelvis. The side face that connects the recess and the exterior surface may be flat or possibly inwardly sloping towards the recess, which is preferably approximately centered in the side face.

The prosthesis stem and the cup may be fixed to the femur and the pelvis respectively by using cement, or through a cement-free force fit. The invention may be used with both fixation techniques.

When replacing a worn out hip with a prosthesis, the head of the femur is replaced. This is done by cutting the neck of the femur and hollowing out the top of the femoral canal in order to make room for the elongated prosthesis stem that is either cemented into the hole or force fitted.

The cavity on the pelvis is milled out to receive the cup, which is then fixed either by means of cement or a force fit.

If the ball head is detachable, this is placed on the prosthesis stem before the ball head is placed in the cup, the joint is assembled by lifting the patient's leg up to a natural position and inserting the ball head in the recess in the cup, whereupon the incision is closed.

Such a prosthesis should give the patient a mobility that approximates that which is provided by the natural joint. However, as the joint capsule etc. is removed during the operation, it is possible for the patient to place the leg in a position outside its normal freedom of movement. This may cause the head of the prosthesis to jump out of the cup (luxation). Moreover, it is important that a "natural" movement of the joint does not cause the patient to get in a situation where the leg ends up in positions where the neck of the prosthesis rides on the edge of the cup. This happens through simple leverage. Luxation occurs in the case of between about 2 and 9% of all patients who have had a femoral prosthesis put in. If this happens, the patient must be anaesthetized before the joint is put back into place. Some patients must have a new operation. The risk of luxation is much greater in patients whose prosthesis components are assembled so as to have an incorrect mutual positioning, than in those where the mutual positioning of the components is correct.

The inventor has previously shown that an optimum mutual relationship between the prosthesis stem and the cup under experimental conditions (not published) results in a reduced risk of luxation because the patient can go through the everyday natural range of motion (ROM) without the parts of the prosthesis ending up in such mutual positioning so as to entail a risk of luxation.

The inventor has previously shown (not published) that the most adequate ROM is achieved by assembling both prosthesis components in a manner so as to give them a forward angle of about 15 degrees relative to the frontal plane of the body, while the cup forms an angle of 45 degrees with the horizontal plane. In medical terminology, forward angling is termed anteversion, whereas a backward angling is termed retroversion. An angle greater than 45 degrees relative to the horizontal plane when the patient is standing, is termed abduction, whereas an angle less than 45 degrees is called adduction.

The inventor has also previously shown (not published) that even though the optimum is to have each of the components angled forwards at 15 degrees, the result is nearly as good if the sum of the forward angling of the two components is 30 degrees. Thus a prosthesis joint where the cup is angled forwards at 10 degrees and the prosthesis stem is angled forwards at 25 degrees will result in a ROM for the patient that is nearly as adequate as if both components were angled forward at 15 degrees, the sum of the forward angling being 30 degrees for both cases.

During the fastening of the prosthesis stem accurate alignment of the prosthesis stem in the femur may be difficult in practice, especially if the stem is to be fastened cement free. Due to the shape of the internal channel in the femur, the prosthesis stem has a tendency to slide into the milled channel in the femur resisting to be forced into a specific angle.

Several solutions are known for insertion of the prosthesis stem in the cup and to ensure that the individual part is being fixed correctly.

A device for alignment and for holding the cup as it is cemented into the pelvis is known from U.S. Pat. No. 5,976,149. The temporary holding device for the cup is temporarily fixed to the pelvis during the cementation.

From GB 2,197,790 a device for assuring that the cup in an artificial hip joint is fixed with a predetermined anteversion and a predetermined angle to the horizontal plane, is known. The mutual angle between the parts in the prosthesis is not taken care of by using this device.

Instruments for insertion of the cup are described in EP 888,759 A1 and U.S. Pat. No. 5,540,697. These instruments are handles onto which the cup is fastened during the insertion but they do not have any means for assuring the correct position and direction of the cup. It is up to the individual surgeon and his experience to determine.

Several devices and means for assuring the alignment of the prosthesis stem during the insertion into the femur are known from EP 207 873, PCT/DE90/00715 and EP 865 776 A2. As mentioned this fixation is not critical. Additionally, these publications only describe devices and means for insertion of one of the prosthesis parts, i.e. the prosthesis stem, and do not describe any means to ensure an intended mutual angle between the cup and the prosthesis stem.

PCT/NO00/00299, having the same inventor as the present application, describes a tool to set the intended mutual angle between the prosthesis stem and the cup during the cementation of the cup in the pelvic cavity. The tool described may be locked relatively to the prosthesis stem and has one or more abutment surface(s) designed to rest against a surface of the cup so that the parts are locked relative to each other. Preferably the prosthesis is fixed to the channel I femur firstly, before the leg of the patient and the prosthesis stem is placed in a normalized position and is used to position the cup correctly. This device, however, may not be used by itself to assure the mutual positioning between the prosthesis parts when using cups to be mounted without the use of cement. Additionally it may only be used to assure that the parts of the prosthesis are positioned correctly relative to each other, but does not take into consideration the correct insertion relative to the patient.

Today there are no means available to ensure that the surgeon installs the prosthesis components with this correct mutual relationship. With today's methods therefore, this is done as judged by the eye. This judgement may be sufficient, especially for experienced surgeons who carry out a considerable number of this type of operation each year. It is estimated that surgeons who do less than 20 of these every year carry out 80% of all implantations of artificial hip joints. This number is not sufficient to get enough practice.

The bone coverage for the cup is often inferior when the cup is correctly mounted. The surgeon will often in cases like that choose to depart from the normally desired angle for the cup to get better bone coverage. In these cases it would be of great advantage if the surgeon could measure the actual angle and thus be able to choose the best compromise between angle and bone coverage.

It is therefore desirable to have a method and means that ensure a correct mutual positioning of the main parts of the prosthesis in order to reduce the possibility of errors, and thereby also reduce the risk of luxation with the resulting pain for the patient, and a possible second operation.

During insertion of the artificial hip joint it may also be desirable to adjust the length of the limb by inserting the prosthesis so that the effective length of the femur from the knee to the hip joint is lengthened or shortened. Additionally it may be desirable to adjust offset, i.e. the distance between the length axis of the femur and the sagittal plane of the body.

Today no good and reliable method or tool for reliable adjustment of the length of the limb or offset exists. An adjustment of the limb length may prevent consequential damage in the back, whereas an incorrect offset may reduce the vigor considerably as the attachment angle or the muscle leverage is incorrect. Thus, both errors may cause considerable pain and danger for consequential damage to the patient.

SUMMARY

The desired regulation of the offset or the desired final offset and length of the limb will be determined during a pre-operative examination and polyclinical study of the patient.

It is a goal for the present invention to provide a tool, a system and a method to assure that the prosthesis is correctly inserted, that the components of the prosthesis are assembled having the correct mutual angle and to assure the provision of a correct control of the length of the limb and offset.

Other goals for the present invention will be apparent by reading the following description.

According to a first aspect of the invention a method of ensuring the desired mutual positioning of the main components of an artificial hip joint prosthesis, i.e. a prosthesis stem with a ball head and a cup with a recess for receipt of the ball head comprising a tool for interaction with a neck of the prosthesis stem and a cup so that the angle between the prosthesis stem and cup may be controlled, wherein one or more indicators is placed at the positioning tool which position and orientation in the room may be read by means of an instrument for determination of the position in the room, is provided.

It is preferred that the instrument determination of position in the room comprises a detector fastened to the patient's pelvis.

It is also preferred that the instrument for determination of the position in the room comprises a conversion unit for conversion of the position of the indicator or indicators in the room to the angles in question.

Preferably the instrument for determination of the position additionally comprises an indicator to be fastened to the femur for measuring the spatial angle, the offset and the length of the limb.

According to a preferred embodiment the instrument for determination of the position is an instrument comprising a source for a magnetic field, one or more sensors and a calculation unit, and a display unit for presentation of the position of the sensor(s).

It is preferred that the instrument for determination of position in the room comprises a conversion unit for conversion of the spatial position of the indicator or indicators to the desired angles.

According to a second aspect of the present invention there is provided a method for computer assisted insertion of an artificial hip joint where the anatomy of the hip is made available in a conventional way and the femur and the pelvis is prepared for insertion of the parts of the prosthesis, where the method comprises the following steps:

a) the parts of the prosthesis, i.e. a prosthesis stem and a cup are temporarily inserted into the femur and the pelvis respectively, b) a positioning tool for controlling the angle between the parts of the prosthesis is inserted between the prosthesis stem and the cup, c) the joint is put together, the patient's hip and knee is stretched and the foot is placed so that the toes are pointing forward relative to the patient's body, d) the position of the parts of the prosthesis is measured by means of an instrument for determination of the position, e) the joint is luxated and the components of the prosthesis are removed, f) the cup is again inserted into the pelvis and it is controlled by means of the system for determination of position that the position of the cup is the same as under d), g) the cup is fixed in this position, h) the prosthesis stem is fixed to the femur, and i) the joint is again put together and the operation is concluded in a conventional way.

It is preferred that the instrument for determination of the position comprises one or more sensors and a conversion unit that calculates the spatial position of the detector(s).

It is also preferred that a sensor that is placed on the position tool during step d) is placed on an instrument for insertion of the cup in step f).

According to a preferred method a second sensor is fastened to the pelvis of the patient after the anatomy is made available, for correction of any movement of the pelvis during the operation.

It is also preferred that a third sensor is fastened to the femur of the patient for determination of the position of the femur and wherein the preoperative offset and length of the limb is measured after step c) but before step e) by measuring the distance between the second and third sensor.

It is also preferred that the desired offset and length of the limb is measured and optionally corrected before step h).

The invention also comprises a method for computer assisted insertion of an artificial hip joint where the anatomy of the hip is made available in a conventional way and the femur and the pelvis is prepared for insertion of the parts of the prosthesis, where the method comprises the following steps:

j) the parts of the prosthesis, i.e. a prosthesis stem and a cup are temporarily inserted into the femur and the pelvis respectively, k) a positioning tool for controlling the angle between the parts of the prosthesis is inserted between the prosthesis stem and the cup, l) the joint is put together, the patient's hip and knee is stretched and the foot is placed so that the toes are pointing forward relative to the patient's body, m) the position of the parts of the prosthesis is measured by means of an instrument for determination of the position, n) the joint is luxated and the components of the prosthesis are removed, o) the prosthesis stem is inserted into the femur and it is controlled by means of the system for determination of position that the position of the stem relative to the femur is the same as under step m), p) the prosthesis stem is fixed in this position;

q) the cup is inserted into the pelvis and it is controlled by means of the system for determination of the position so that the cup has the same position relative to the pelvis as under step m)

r) the cup is fixed in this position, and s) the joint is again put together and the operation is concluded in a conventional way.

It is preferred that the instrument for determination of the position comprises one or more sensors and a conversion unit that calculates the spatial position of the detector(s).

Preferably a sensor that is placed on the position tool during step m) is placed on an instrument for insertion of the cup in step q).

It is preferred that a second sensor is fastened to the pelvis of the patient after the anatomy is made available, for correction of any movement of the pelvis during the operation.

Preferably a third sensor is connected to the femur of the patient to determine the position of the femur and wherein the preoperative offset and preoperative bone length is measured after step l) but before step n) by measuring the distance between the second and the third sensor.

Preferably the desired offset and length of the limb is controlled and is optionally adjusted during step o).

DETAILED DESCRIPTION

The present invention comprises a system including a tool corresponding to the tool described in PCT/NO00/00299 to ensure the correct mutual position between the parts in an artificial hip prosthesis and a tool for precise determination of position of a number of sensors.

The apparatus for determination of position (position determination instrument) may be of any type and from any producer. As an example a magnetic indicator and a device for magnetic measurement of position (Isotrack II from Polhemus Navigation Science, USA, or Flock of Birds® from Ascension Technology Corporation, Burlington, Vt., USA), or a video based apparatus for measurement of bearings (e.g. from HipNav from Casurgica, Inc, or Medivision from Stratec Medical) where the positions are calculated by a video-based cross bearing, may be used. The apparatus for determination of position is preferably connected to a conversion unit for calculating the angles for fixation of the cup relative to a plane of reference. The presently preferred system for determination of position is the system Flock of Birds®. This system comprises a transmitter, or a source for a magnetic field located at a suitable place close to the patient, a plurality of sensors and a central unit having a standard computer interface. Flock of Birds® is constructed to operate with a plurality of sensors independent of each other, where the sensor's co-ordinates, angle and rotation relative to a co-ordinate system defined with a basis in the transmitter, are given with very high degree of accuracy. In connection with the present invention, the Flock of Birds® system is preferably connected to a (conversion unit) computer for calculation of the desired angles and for displaying a user interface that is suitable for an operation.

The phrase "system for determination of position" as used in the present application is used to indicate the Flock of Birds® system or an equivalent system. Additionally, equipment traditionally used for this kind of operations is used.

Figure 1:
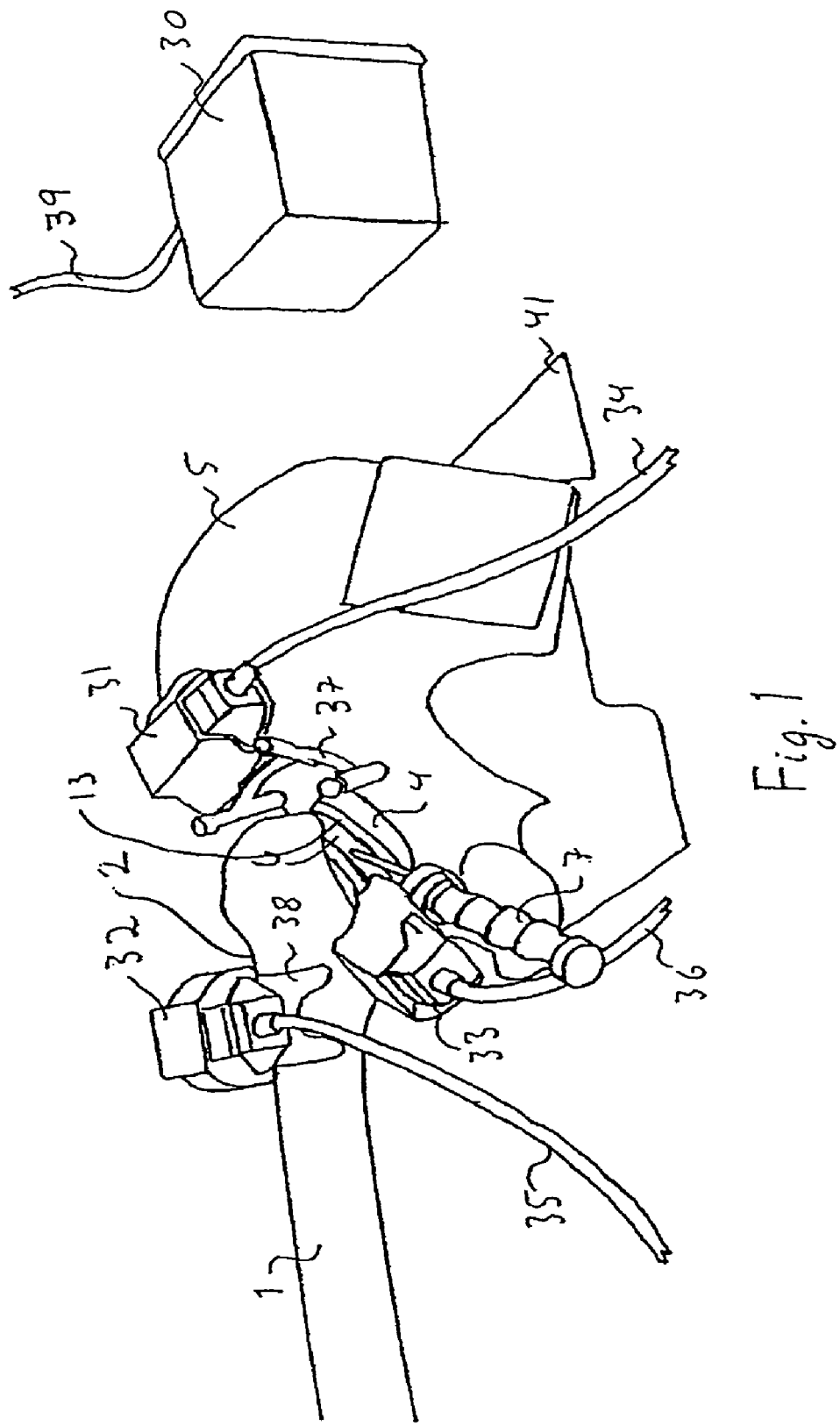
FIG. 1 illustrates a model of the pelvis and a femur where the hip joint is replaced by an artificial hip joint and where sensors for measurement of preoperative offset are mounted on both.
Figure 2:
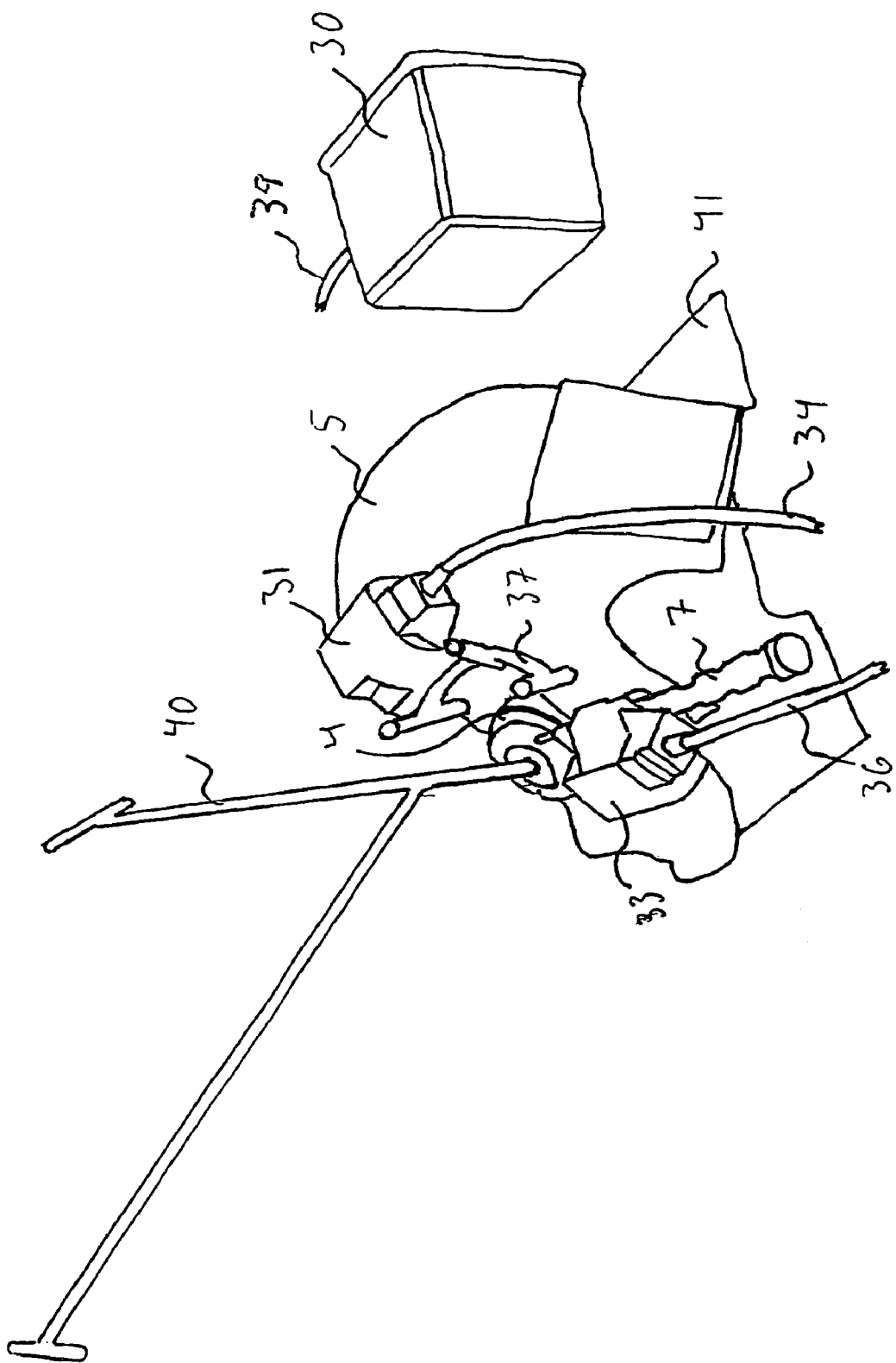
FIG. 2 illustrates a model of the pelvis during insertion of a cup of a prosthesis.

The FIGS. 1 and 2 illustrate two different steps in an operation for insertion of an artificial hip prosthesis and the localization of the different tools and sensors on a model of a half pelvis placed on a rack.

The normal procedure for insertion of an artificial hip prosthesis by means of the present tool and system will be as follows, without being bound by the described sequence of the steps:

1. The patient is examined and a plan for any adjustments of the length of the limb or offset is made. This is preferably done pre-clinically.

2. When the patient is made ready for operation he is placed on the operation table in the position of a tin soldier.

3. A transmitter 30 is fastened to a rack at the operation table and three sensors 31, 32, 33 connected to the system by means of cables 34, 35, 36, are placed in sterile camera bags.

4. Surgical cuts are made and the anatomy of the hip is made available.

5. A fastening device 37 for a sensor is fastened to the pelvis 5 and the first sensor 31 is fastened to the fastening device 37.

6. A fastening device 38 for a sensor is fastened to the upper part of the femur 1 and the second sensor 32 is fastened thereto.

7. The pre-operative length of the limb and offset is measured between the sensors 31 and 32 and the results are saved in a PC connected to the positioning system.

8. Thereafter the standard operational procedures for replacement of a hip joint are followed, such as opening of the joint-capsule, sawing through the neck 2 of the femur, the marrow of the femur 1 is hollowed out and the joint cavity at the pelvis 5 is milled out to prepare them to receive the components of the prosthesis.

Figure 3:
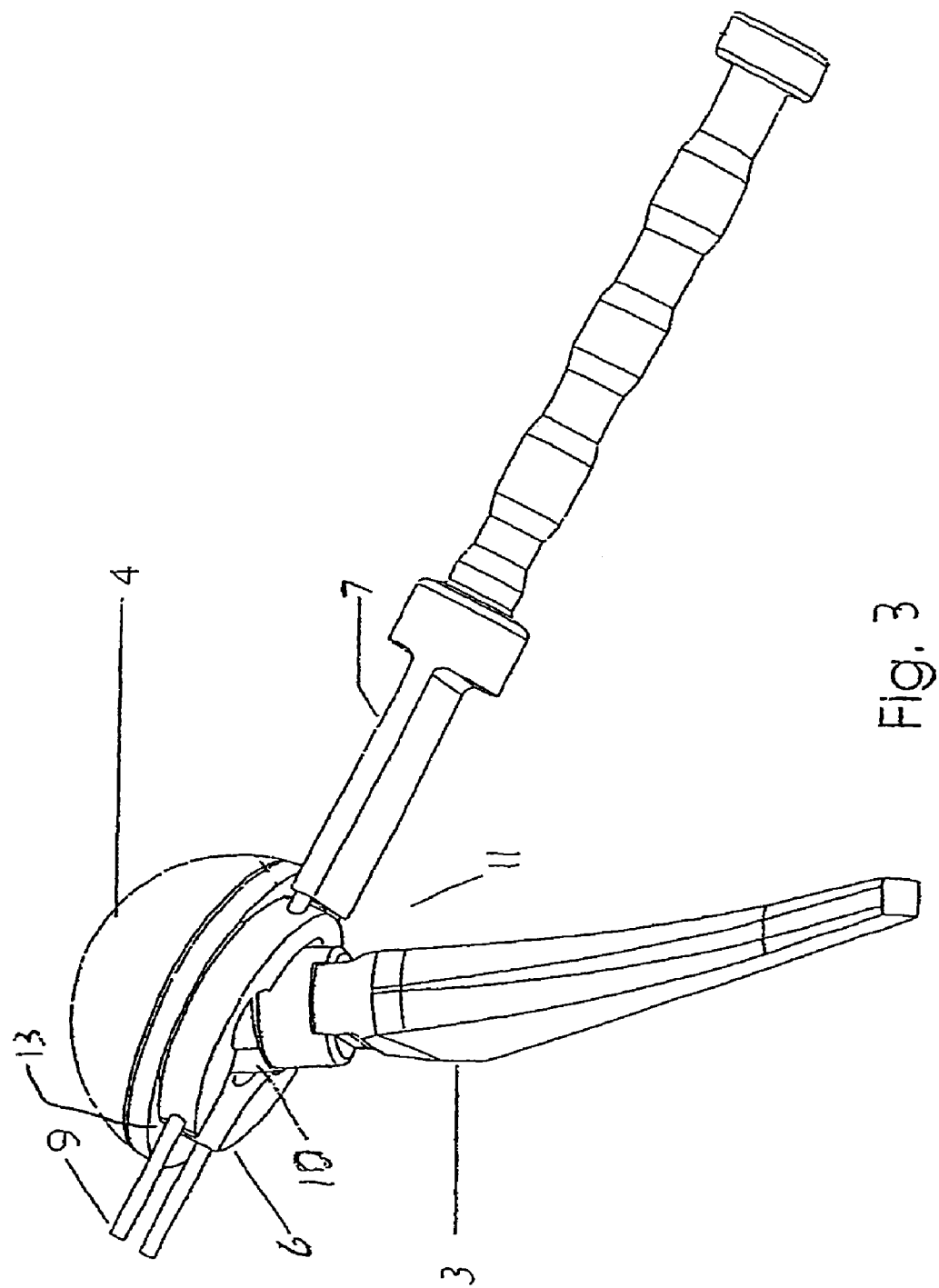
FIG. 3 illustrates an artificial hip joint put together with an anteversion head.
Figure 4:
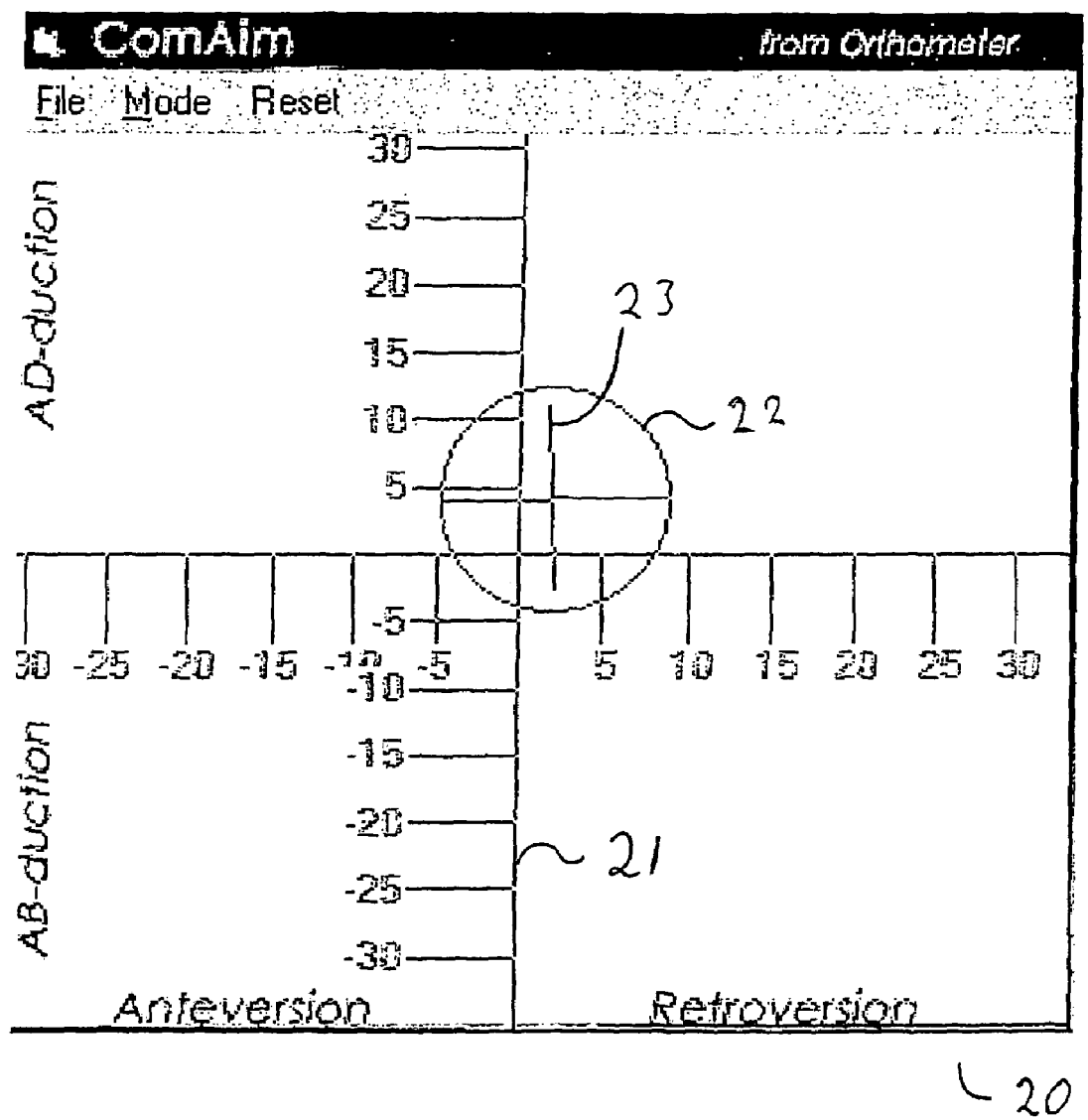
FIG. 4 is an exemplary display for adjustment of the angle of the inserting tool relative to the pelvis.

9. A prosthesis stem 3 is temporarily placed in the prepared hollow in the femur 1. An anteversion head, as illustrated at FIG. 3, is placed at the prosthesis stem 3, a provisional ball 10 and a collar 6 is placed at the prosthesis neck, which is an elongation of the prosthesis stem 3. The collar 6 and the provisional ball 10 is locked together by means of guide rods 9 placed on a grip 7, where the guide rods run through both the ball 10 and the collar 6. The collar 6, the ball 10 and the guide rods 9 constitute a tool 11 for control of position that defines the angle between the cup and the prosthesis stem when the ball 10 lies in a corresponding recess in the cup 4 and the collar 6 rests against a side face 13 of the cup 4.

10. A cup 4 is temporarily placed in the milled out cavity in the pelvis and the artificial joint is put together. The hip and knee are stretched so that the toes are pointing forwards and parallel to the toes of the other foot. Thereafter the length of the limb and offset are measured the same way as the measurement of preoperative length of the limb and offset. The measured values are compared with the desired values according to the preoperative plan. Any deviations from the preoperative plan are thereafter adjusted.

11. Sensor 33 is then placed at the handle 7 of the anteversion head and the co-ordinates, direction and angle of the sensor are measured and saved in the PC connected to the positioning system. The anteversion head assures that the mutual position of the sensor 33 at the handle 7 and the cup is fixed. A measurement of the measuring values for the sensor 33 would therefore indirectly indicate the position of the cup relative to the co-ordinate system. This measurement is used as reference for the final fixation of the cup and correspondingly for the prosthesis stem. FIG. 1 illustrates this step in the operation where the femur is placed so that offset and the length of the limb may be measured at the same time as the sensor 33 is placed at the handle to measure the correct position for the cup 4.

12. The joint is again luxated and the prosthesis parts are taken out. The cup is then put on an insertion handle 40 and the handle 7 is transferred to the insertion handle. The insertion handle 40 is of a standard type routinely used for this kind of operation, having a minor adaptation to be able to receive the handle in a position corresponding to the position of the handle relative to the cup when the handle is placed on the anteversion head. The adaptation is made by drilling two holes to receive the guide rods 9 of the insertion handle 7.

Figure 5:
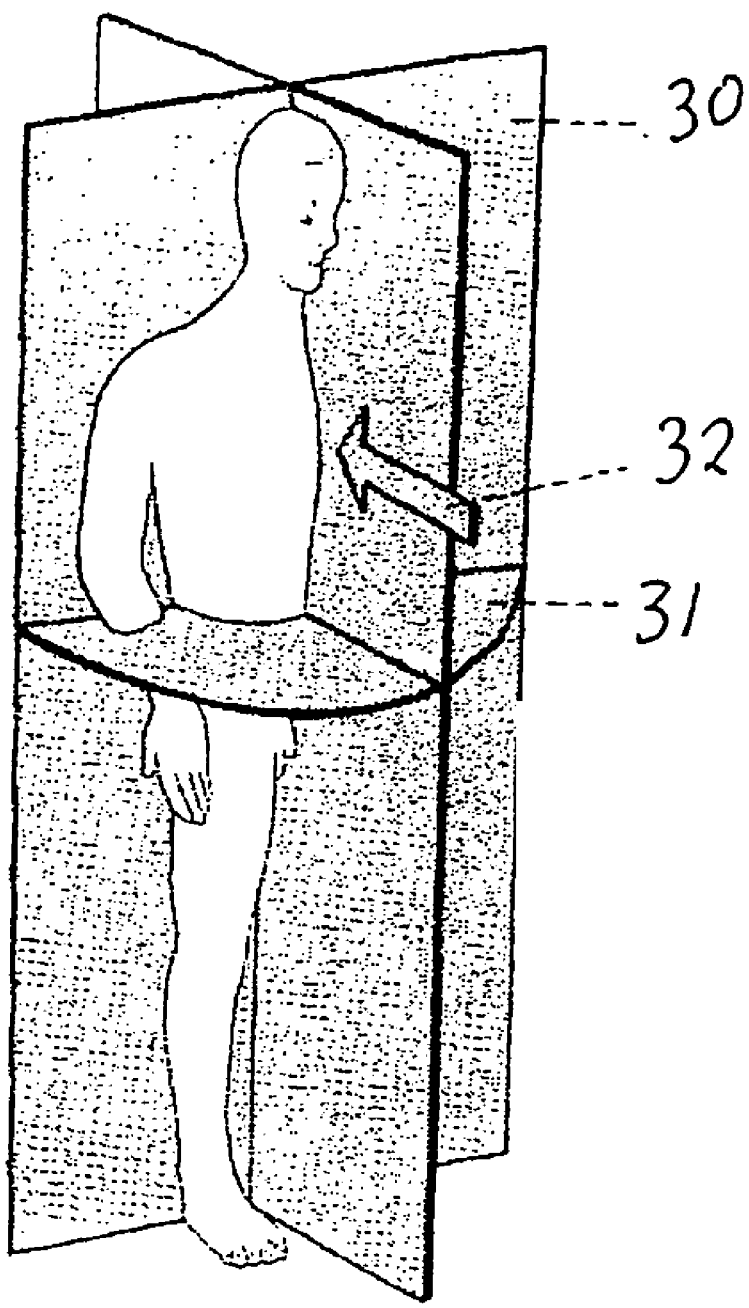
FIG. 5 illustrates the patient's planes that are used to define the angles.

13. The cup is thereafter installed by means of the insertion handle. The measured values for the position of the sensor 33 relative to the sensor 31 at the pelvis is displayed at a display 20 as illustrated in FIG. 5. The above measured reference value for the temporary insertion of the prosthesis parts is shown at the screen as origin in a co-ordinate system and the deviation from the reference value is given in degrees along the co-ordinates. Anteversion and retroversion, respectively, are indicated along the z-axis, whereas abduction and adduction, respectively, are given along the Y-axis.

14. The values measured for sensor 33 are shown as a circle 22 with cross hairs 23. When the cross hairs 23 overlap with the co-ordinate system 21, the cup 4 is in the same position as during the measurement of the reference value. Departure from the reference value may be controlled as desired by the surgeon taking into consideration bone coverage etc. After the desired position is achieved, the cup may be fixed e.g. by means of cement. FIG. 2 illustrates this step for adjustment and fixation of the cup 4 to the pelvis.

15. The prosthesis stem is thereafter fixed permanently to the femur, a permanent ball is put onto the prosthesis neck and the joint is put together.

16. The operation is finished by means of conventional technique.

In an alternative procedure for insertion of an artificial hip joint the prosthesis stem may be fixed to the femur based on data for the position of the prosthesis stem provided in a modified step 11 above. This modified step 11 is based on the setup illustrated in FIG. 1. Measurements of the sensor 32 relative to sensor 31, sensor 33 relative to sensor 31 and sensor 33 relative to sensor 32, are taken. The position of the prosthesis stem relative to the sensor 32 is thereby given as the sensor 33 is fixed relative to the prosthesis stem. The positioning tool 11 may then be used together with the system for determination of the position to recreate this relative position, and if necessary make the desired correction in offset and length of the limb during the insertion and fixation of the prosthesis stem in the femur. The cup 4 may be independently inserted in the pelvis as indicated above. The desired positioning of both the prosthesis stem and the cup is assured by this procedure.

The angle calculated by means of the conversion unit mentioned above, is an angle relative to a reference plane. It may be practical to refer to the patient's frontal plane 30. It is, however, important that the plane is clearly defined and is suitable for alignment of prosthesis parts for an artificial hip joint. One skilled in the art will understand which planes are useful in practice.

According to a preferred embodiment the basic angle is generated using this plane, i.e. the angle measured using the positioning tool where the cup 4 has the desired angle and where the prosthesis stem, and thereby also the patient's leg, has the same angle relative to the cup, by means of a co-ordinate system 21 at a screen 20 as illustrated in FIG. 5. This co-ordinate system is locked to give basic angle or the angle to be used for insertion of the cup and correspondingly for the prosthesis stem.

After calculation of the correct angle and the co-ordinate system is locked as stated above, the patient's femur is moved so that the positioning tool 11 and the provisional cup are removed from interaction with the milled recess in the patient's pelvis. A cup 4 to be permanently fixed in the milled recess is then placed on the insertion tool 12.

The insertion tool 12 is adapted for interaction with the recess in the cup 4 and has a contact surface designed for contact with the side surface of the cup. The handle 7 with guide rods 9, that is removed from the positioning tool 11, is then fastened to the insertion tool 12 in holes for the guide rods 9 (not illustrated). After fixing the handle 7 to the insertion tool 12 the mutual position between the cup and the indicator 33 will be the same as it was when using the positioning tool 11. By aligning the positioning tool so that the original position for the indicator is recreated it is possible to assure that the cup has the same position relative to the pelvis as the provisional cup had during the measurement using the positioning tool 11. Thereby it is possible to assure that the cup 4 of an artificial hip joint is correctly inserted into the pelvis and that the mutual angle between the parts of an artificial hip joint is correct.

By using the tool as described above, wherein the angle measured by means of the tool for control of position was shown as a co-ordinate system 21, the position of the indicator is now indicated and the angle of the insertion tool are thereby shown indirectly as a circle 22 with cross hairs 23. The insertion tool 12, handle 7 and indicator 33 are then moved so that the cross hairs 23 coincide with the co-ordinate system 21. When the cross hairs 23 coincide with the origin of the co-ordinate system 21, the angle of the insertion tool is correct and the cup may be fixed, either by pounding/pressing the cup to fit into the milled recess or by cementing.

The co-ordinate system is all the time controlled and corrected relative to the sensor 31 fastened to the pelvis, so that minor movements in the patient's pelvis between the determination of the angle and insertion, are corrected.

The insertion tool may be of different design. The illustrated tool is a tool that is commonly used for a cemented prosthesis. A tool for an uncemented prosthesis must have an impact surface where the surgeon may pound during the insertion of the prosthesis in addition to be adapted for engagement with the cup. The insertion tool may also have a replaceable contacting surface for the cup so that the contacting surface may be changed to adapt the tool to the actual cup. During the insertion of an uncemented prosthesis a provisional cup has to be used for the reference measurement.

After the cup is fixed at the correct place and in the correct position, the insertion tool 12 may be removed, a permanent ball is put on the prosthesis neck, the femur is placed in the normal position so that the artificial joint is put together before the operation is finished the conventional way.

In these circumstances the surgeon using the present tool has the possibility to freely depart from the ideal angle providing special circumstances. Such special circumstances can, for example, be the fact that the bone coverage for the cup is inferior for the ideal angle. If this is the case, the surgeon may choose another angle being a compromise between the ideal angle and the need for the best bone coverage possible. The deviation may then be read, introduced into the journal and can be used when the patient is given advice after the operation on the permitted movements.

According to an alternative embodiment of the present invention, the positioning tool may also be used to ensure a correct direction for the milling in the pelvis and to ensure that any conflicting bone mass around the joint hollow is removed, if it causes impingement. After the measurement of the desired angle as described above by means of the positioning tool, the handle 7 with the indicator 33 is placed on the mill. The desired angle is again found by means of the tool for determination of the angle before the mill is started. It is here possible to read the angle continuously to see if the angle is correct during the milling operation.

The determination of the angle by means of the present tool is, as described above, an indirect determination where an indicator 33 is located on a handle 7 and the position of the indicator in the room is used for the determination of an angle. It is therefore practical to move this handle with the indicator from the positioning tool 11 to the insertion tool 12 and possibly to the mill. Preferably the handle with an indicator may be placed at the insertion tool or possibly at the mill to achieve the same distances and angles to the cup and the mill respectively as during the measurement.

It is not a condition for the present invention that the indicator 33 is placed at the handle 7. The indicator 33 may have any suitable localization. If the indicator is medically acceptable, one or more indicators may, as an example, be integrated with the prosthesis stem. In this case it may be practical to integrate one or more indicator(s) in a corresponding position relative to the prosthesis cup with the insertion tool.

Also solutions where the indicator at the positioning tool has a different geometric location than the indicator at the insertion tool are possible. In these cases, a conversion of the position of the indicator at the insertion tool corresponding to the indicator at the positioning tool is necessary. The conversion may be one automatically based on the measurements of the different tools and the position of the indicators at the tools.

Other units for calculation, such as a PC or a different computing device with a program for conversion of the measured values to units and forms for representation that are more suitable for a user-friendly presentation on a screen or another display unit, may be connected to the instrument for determination of the position. Several units of the kind are available on the market and the possibilities for adaptation are great. The inventor has used a form of representation where the first measured position and the angles relative to a reference plane derived therefrom are represented at a screen by means of a co-ordinate system and where the corresponding angles when using the insertion tool is represented at the screen as cross hairs. This has been found to be very practical.

A preferred embodiment of the present invention is described above. In cases where the control and possible adjustment of offset and length of the limb are without interest the sensor 32 and the step for controlling these parameters may be omitted.

The sensor 31 is preferred as it makes it possible to correct any displacement of the pelvis during the operation between the measurement of the reference values and the fixation of the cup respectively, between the measuring of the preoperative offset and length of the limb. It is also possible to practice the present invention without a sensor 31 fixed to the pelvis. The results will, however, be more uncertain than by using the sensor, provided that no other way of ensuring the position of the pelvis and to prevent movement of the pelvis between the measurements are available. The co-ordinate system will then be defined by the transmitter without any corrections from a reference sensor fixed to the pelvis.

Additionally, different variations of the method described above are possible without leaving the scope of protection defined in the attached claims.

The anteversion head 11 with a handle and sensor 33, may as an example, be used for insertion of the prosthesis stem into the femur. The position of the sensors 33 and 32 relative to each other, then has to be measured in step 11 above, in addition to the other measurements performed during step 11. During the insertion of the prosthesis stem the relative localization of the sensors 31 and 33, if necessary corrected for length of the limb and offset as described above for the insertion of the cup, is recreated before the prosthesis stem is fixed. This controlled and guided insertion of the prosthesis stem may be carried out before or after the insertion and fixation of the cup.

The angles in question used above are ideally measured relative to the planes of orientation indicated in FIG. 6. The patient's frontal plane 30 is approximately parallel to the bed when the patient is lying flat on the back, the horizontal plane 31 is approximately parallel to the ground when the patient is standing upright and the sagittal plane is perpendicular to both planes through the body's long axis.

The indications of angles through the present description and claims are approximations relative to the planes of orientation given in FIG. 6 and are therefore indicated relative to each other. A determination of the angles relative to the body's planes of orientation is desirable but inaccuracies due to tissue such as muscles and adipose tissue, unknown bending angle in the pelvis and unknown degree of bending in the backbone in the lying position, makes it possible only to achieve approximations of the final angles relative to the planes of orientation. The best possible approximation is achieved by stretching out the hip and thereafter measuring the relative angle by means of the positioning tool 11 described above. It is, however, important in using the present invention that the patient is lying in exactly the same position during the measurement of the angle and locking of the co-ordinate system by means of the positioning tool 11, as during the insertion of the cup. In this way a sufficiently good approximation of the ideal angles is achieved.

What is claimed is:

1. A method for computer assisted insertion of an artificial hip joint prosthesis comprising:
    making the anatomy of a hip available for insertion of parts of said prosthesis, wherein said parts of said prosthesis comprise a prosthesis stem and a cup;
    preparing for insertion of said parts of said prosthesis;
    inserting temporarily said prosthesis stem into a femur;
    inserting temporarily said cup into a pelvis;
    inserting a positioning tool between said prosthesis stem and said cup, said positioning tool configured to control an angle between said parts of the prosthesis;
    assembling the artificial hip joint;
    stretching said hip and a knee associated with said hip;
    placing a foot associated with said hip and said knee in a position configured with the toes pointing forward relative to a body associated with said foot;
    measuring the position of said parts of the prosthesis with a position determination instrument;
    luxating the hip joint;
    removing said parts of the prosthesis from said femur and said pelvis;
    inserting said cup into said pelvis into a predetermined position, said predetermined position being equal to a position measured by said position determination instrument;
    controlling said insertion of said cup with said position determination instrument;
    fixing said cup into said predetermined position;
    fixing said prosthesis stem to said femur; and
    reassembling said hip joint.

2. The method of claim 1, wherein said position determination instrument comprises at least one sensor and a conversion unit configured to calculate the placement and spatial position of an at least one first sensor.

3. The method of claim 2, further comprising:
    placing said at least one first sensor on said positioning tool; and
    moving said at least one first sensor to an insertion instrument for the insertion of said cup.

4. The method of claim 2, further comprising:
    fastening a second sensor to said pelvis after the anatomy is made available; and
    correcting for any movement of said pelvis during the method for computer assisted insertion of the artificial hip joint with said second sensor.

5. The method of claim 4 further comprising:
    fastening a third sensor to said femur, said third sensor is configured for use in the determination of the position of the femur;
    measuring a preoperative offset and a length of a limb of said femur subsequent to said hip joint assembly and prior to luxation of said hip joint assembly, wherein said measuring comprises measuring a distance between said second sensor and said third sensor.

6. The method of claim 5 further comprising:
    measuring said predetermined position before fixing said prosthesis stem to said femur; and
    correcting said predetermined position before fixing said prosthesis stem to said femur.

7. A method for computer assisted insertion of an artificial hip joint prosthesis comprising:
    making the anatomy of a hip available for insertion of parts of said prosthesis, wherein said parts of the prosthesis comprise a prosthesis stem and a cup;
    preparing for insertion of said parts of the prosthesis;
    inserting temporarily said prosthesis stem into a femur;
    inserting temporarily said cup into a pelvis;
    inserting a positioning tool between said prosthesis stem and said cup, said positioning tool configured to control an angle between said parts of the prosthesis;
    assembling the artificial hip joint;
    stretching said hip and a knee associated with said hip;
    placing a foot associated with said hip and said knee in a position configured with the toes pointing forward relative to a body associated with said foot;
    measuring the position of said parts of the prosthesis with a position determination instrument;
    luxating the hip joint;
    removing said parts of the prosthesis from said femur and said pelvis;
    inserting said prosthesis stem into said femur in a predetermined position, said predetermined position being equal to a position measured by said position determination instrument;
    controlling said insertion of said prosthesis stem with said position determination instrument wherein said femur is placed into said predetermined position;
    fixing said prosthesis stem to said femur in said predetermined position;
    inserting said cup into said pelvis into a predetermined position, said predetermined position being equal to a position measured by said position determination instrument;
    controlling said insertion of said cup with said position determination instrument;
    fixing said cup into said pelvis in said predetermined position; and
    reassembling said hip joint.

8. The method of claim 7, wherein said position determination instrument comprises at least one sensor and a conversion unit configured to calculate the placement and spatial position of an at least one first sensor.

9. The method of claim 8 further comprising:
placing said at least one first sensor on said positioning tool; and
moving said at least one first sensor to an insertion instrument for the insertion of said cup.

10. The method of claim 9 further comprising:
fastening a second sensor to said pelvis after the anatomy is made available;
correcting for any movement of said pelvis during the method for computer assisted insertion of the artificial hip joint with said second sensor.

11. The method of claim 10 further comprising:
fastening a third sensor to said femur, said third sensor is configured for use in the determination of the position of the femur;
measuring a preoperative offset and a preoperative length of a said femur subsequent to said hip joint assembly and prior to luxation of said hip joint assembly, wherein said measuring comprises measuring a distance between said second sensor and said third sensor.

12. The method of claim 11 further comprising:
controlling a predetermined preoperative offset determined from said measurement;
controlling a predetermined preoperative femur length determined from said measurement
adjusting said predetermined preoperative offset during inserting said prosthesis stem into said femur; and
adjusting said predetermined preoperative femur length during inserting said prosthesis stem into said femur.

* * * * *